United States Patent [19]

Torii et al.

[11] 4,339,607

[45] Jul. 13, 1982

[54] PROCESS FOR PREPARING ANISALDEHYDE

[75] Inventors: Shigeru Torii; Shoji Nakane, both of Okayama; Toshifumi Shirakawa, Koshigaya; Mitsuo Akada, Tokushima, all of Japan

[73] Assignee: Otsuka Kagaku Yakuhin Kabushiki Kaisha, Osaka, Japan

[21] Appl. No.: 170,781

[22] Filed: Jul. 21, 1980

[30] Foreign Application Priority Data

Jul. 30, 1979 [JP] Japan .................................. 54/97481

[51] Int. Cl.$^3$ ............................................. C07C 45/28
[52] U.S. Cl. ..................................... 568/426; 204/91; 204/63
[58] Field of Search ......................................... 568/426

[56] References Cited

U.S. PATENT DOCUMENTS 3,745,180  7/1973  Rennie ............................ 568/426 X

OTHER PUBLICATIONS

Syper, Tetrahedron Letters, 37, (1966), pp. 4493–4498.

Primary Examiner—Bernard Helfin
Attorney, Agent, or Firm—Larson and Taylor

[57] ABSTRACT

Anisaldehyde is prepared by performing at least once the steps of (a) electrolyzing cerium (III) nitrate or ammonium cerium (III) nitrate to obtain water containing cerium (IV) nitrate or ammonium cerium (IV) nitrate and/or a solution of lower alcohol containing the cerium (IV) salt, and (b) oxidizing p-methyl anisole to anisaldehyde with the cerium (IV) salt-containing solution of lower alcohol with or without the water contained therein, or with the cerium (IV) salt-containing water having a lower alcohol admixed therewith.

12 Claims, No Drawings

PROCESS FOR PREPARING ANISALDEHYDE

This invention relates to a process for preparing anisaldehyde.

Anisaldehyde is a compound useful for preparing perfumery, plating agents, drugs and various other chemicals. Although the compound has heretofore been produced by the oxidation of anethole, the starting material, which is a natural product, is not available in steady quantities, with a tendency toward greatly decreasing supplies. While this compound can be synthesized by the formylation of anisole, the process is economically disadvantageous because the starting material is expensive and the process gives a large quantity of useless by-product which causes pollution when discarded.

Heretofore known as processes for preparing anisaldehyde by oxidizing the methyl group on the side chain of p-methyl anisole are a process which uses an oxidizing agent, such as potassium dichromate, potassium permanganate or manganese dioxide, and an air oxidation process which uses a catalyst, such as vanadium pentoxide or cobalt acetate. These processes nevertheless are low in yield, give large quantities of by-products if it is attempted to achieve an improved conversion, entail problems in respect of the treatment of the oxidizing agent used, pollution and toxicity, and involve difficulties in the recovery and regeneration of the catalyst used. Although it is known to use trivalent manganese sulfate in an aqueous solution of sulfuric acid, trivalent manganese sulfate is stable only in concentrated sulfuric acid of at least 70% but is converted to a hydroxide immediately at lower concentrations. It has also been reported to use potassium peroxosulfate in the presence of silver nitrate serving as a catalyst, but no report has been made on the regeneration of the oxidizing agent for reuse in these processes. In fact, it is impossible or extremely difficult to regenerate the oxidizing agent for use in circulation.

Published Unexamined Japanese Patent Application No. 144,697/1975 discloses that p-methyl anisole is oxidized with cerium(IV) sulfate in sulfuric acid to obtain anisaldehyde. Such the resulting cerium(III) salt is not electrolytically oxidizable to an extent suited to reuse, the process employs the complex chemical procedure of converting cerium(III) sulfate with an alkali metal hydroxide and hydrogen peroxide to cerium(IV) hydroxide via cerium(III) hydroxide and hydroperoxide and reacting the cerium(IV) hydroxide with sulfuric acid to obtain cerium(IV) sulfate. The process, however, has the drawbacks of requiring a high reaction temperature and involving a very complex mode of circulation of the cerium salt.

German Offenlegungsschrift No. 1,804,727 discloses oxidation of naphthalene, anthracene or the like with cerium(IV) sulfate or ammonium cerium(IV) sulfate in an aqueous solution of sulfuric acid or nitric acid for the preparation of a quinone, and regeneration of the resulting cerium salt by electrolysis. However, the disclosed rection conditions, if used for the oxidation of p-methyl anisole, are almost unable to give the desired product, namely anisaldehyde, but merely afford products of complex structure.

Tetrahedron Letter, 1966, 4493 reports that anisaldehyde can be prepared quantitatively when p-methyl anisole is reacted at room temperature with a 90% aqueous solution of acetic acid containing ammonium cerium(IV) nitrate. In this case, the product is isolated in the form of the corresponding 2,4-dinitrophenylhydrazone compound. We practiced this process with full care exactly in the same manner as reported for the oxidation of p-methyl anisole. Separation and detailed analysis of the reaction mixture revealed that the process afforded 43% of anisaldehyde, 16% of a quinone compound which appeared to have resulted from the oxidation coupling of the starting material and anisaldehyde formed as a product, and various other by-products of unidentified structure. The same process, when conducted at an elevated reaction temperature of 60° C., afforded 51% of anisaldehyde, 18% of the above-mentioned quinone compound and various other by-products of unidentified structure. Although the oxidation process was further repeated similarly at varying temperatures with aqueous solutions of varying acetic acid concentrations, the process gave many by-products but failed to achieve improved anisaldehyde yields. Thus we have found that there is a limitation on the oxidation of p-methyl anisole to anisaldehyde in an aqueous acetic acid solution.

Bull. Chem. Soc. Japan, 35, 1751–1755 (1962) discloses oxidation of p-xylene with cerium(IV) sulfate to p-tolualdehyde and electrolytic oxidation of cerium(III) sulfate for repeated use. However, nothing is reported about p-methyl anisole. The disclosed process has the drawbacks of being low in current efficiency and in conversion to the desired product and involving a further reduction in conversion or yield as the cerium salt is used repeatedly.

We have found that the optimum reaction conditions for the oxidation of compounds with a cerium salt differ delicately with the kind of the starting material, and that oxidation of p-methyl anisole, when conducted by the processes of the foregoing literature, is unable to give anisaldehyde in satisfactory yields.

An object of this invention is to provide a process for oxidizing p-methyl anisole in a very short period of time to obtain anisaldehyde in a high yield and a high conversion.

Another object of the invention is to provide a process for preparing anisaldehyde with the use of an oxidizing agent which can be regenerated easily, semipermanently and quantitatively for repeated use.

Another object of the invention is to provide a process for preparing anisaldehyde with the use of clean electric energy without giving by-products which are likely to cause pollution.

These and other objects of the invention will become apparent from the following description.

The present invention provides a process for preparing anisaldehyde characterized by performing at least once the steps of (a) electrolyzing cerium(III) nitrate or ammonium cerium(III) nitrate with use of a cathode chamber having contained therein nitrate ion-containing water and/or a nitrate ion-containing solution of lower alcohol and an anode chamber having contained therein water containing the cerium salt and/or a solution of lower alcohol containing the cerium salt to obtain water containing cerium(IV) nitrate or ammonium cerium(IV) nitrate and/or a solution of lower alcohol containing the cerium(IV) salt, and (b) oxidizing p-methyl anisole to anisaldehyde with the cerium(IV) salt-containing solution of lower alcohol with or without the water contained therein, or with the cerium(IV) salt-containing water having a lower alcohol admixed therewith.

With the process of this invention, the desired product can be prepared in high yields and high conversions within a very short period of time from a material which is easily available at a low cost, using an oxidizing agent which can be regenerated semipermanently and quantitatively for repeated use. The process utilizes clean electric energy and does not entail formation of by-products that would cause pollution.

The electrolytic oxidation of this invention is conducted in the following manner, using an anode chamber having contained therein the cerium(III) nitrate- or ammonium cerium(III) nitrate-containing water and/or cerium(III) nitrate- or ammonium cerium (III) nitrate-containing solution of lower alcohol obtained from an oxidation reaction by separating anisaldehyde from the mixture. It is useful to admix a small amount of nitric acid or ammonium nitrate with the contents of the chamber. In combination with the anode chamber, a cathode chamber is used which has contained therein nitrate ion-containing water and/or a nitrate ion-containing solution of lower alcohol. Various compounds are usable as nitrate ion sources, such as nitric acid, ammonium nitrate, sodium nitrate, potassium nitrate, alkyl ammonium salts of nitric acid, etc., among which nitric acid and ammonium nitrate are preferable. Examples of useful lower alcohols are those having 1 to 4 carbon atoms, such as methanol, ethanol, propanol, isopropanol, butanol, sec-butanol, t-butanol, etc., which can be used singly or in admixture. With the present invention, these alcohols are usable as admixed with other organic solvents. Examples of such organic solvents are ethers, such as diethyl ether, tetrahydrofuran and dioxane; nitriles, such as acetonitrile and propionitrile; solvents, such as dimethylformamide and dimethyl sulfoxide; ketones, such as acetone and methyl ethyl ketone; and esters, such as ethyl acetate and methyl propionate.

The electrolytic oxidation of the invention is conducted in the above two chambers, which may be used without any diaphragm. However, the chambers are preferably separated by a porcelain diaphragm, ion exchange diaphragm or the like. The electrolytic oxidation quantitatively affords water containing cerium(IV) nitrate or ammonium cerium(IV) nitrate and/or a solution of lower alcohol containing the cerium(IV) salt. The current density for the electrolysis is not particularly limited and is determined as desired in accordance with the size of the electrolytic cell, reaction time, etc. The electrodes can be of any known material, such as platinum, iron, stainless steel, carbon, titanium oxide, lead oxide, lead dioxide or the like. The electrolytic reaction, which can be conducted at a temperature of about 0° to about 100° C., may preferably be conducted at about 10° to about 60° C. The electrolytic reaction oxidizes cerium(III) nitrate or ammonium cerium(III) nitrate alone with a current efficiency of almost 100% for use in circulation without causing any change to the lower alcohol, etc.

p-Methyl anisole is oxidized with the cerium(IV) nitrate- or ammonium cerium(IV) nitrate-containing solution of lower alcohol thus obtained with or without water incorporated therein. When the electrolysis gives an aqueous solution of the cerium(IV) salt, the solution is used as the oxidizing agent with a lower alcohol admixed therewith. In view of the yield and the solubility of the cerium (IV) salt, such oxidizing solutions preferably contain about 20 to 100% by weight of the lower alcohol based on the whole amount of solvent or solvents.

Although the solutions placed into the anode and cathode chambers for electrolysis need not always contain a lower alcohol, the cerium(IV) salt-containing solution obtained from the electrolysis for use as the agent for oxidizing p-methyl anisole must always contain a lower alcohol. While the reason why the oxidizing agent must have the alcohol incorporated therein still remains to be fully clarified, the oxidation of compounds with the cerium salt is delicately influenced by the kind and properties of the compound, oxidation conditions, the properties of the desired product, etc. as already stated and is also affected by the solvent and potential at the site of oxidation. Our research on various conditions has matured to this invention.

According to this invention, p-methyl anisole is oxidized to anisaldehyde usually at a temperature of about −10° to about 60° C., preferably about 0° to about 50° C. The reaction can be completed in a short period of time. With an increase in the proportion of water in the oxidizing solution, by-products, such as coupling product, are more likely to result.

When the reaction solvent used permits extraction of the desired product, the product can be isolated by extraction. Generally the solvent is distilled off completely from the reaction mixture, which is then subjected to distillation or extraction to obtain the product. The remaining solution containing cerium(III) nitrate or ammonium cerium(III) nitrate is placed into the anode chamber of an electrolytic cell, with water and/or a lower alcohol admixed therewith when so desired. With nitrate ion-containing water and/or a nitrate ion-containing solution of lower alcohol further placed in the cathode chamber of the cell, the cerium salt is electrolytically oxidized in the manner already described.

With the present invention, the electrolytic oxidation step and the p-methyl anisole oxidation step are conducted at least once to afford anisaldehyde in a high yield. The invention has the outstanding advantage that even when these steps are repeated a large number of times, the desired product can be produced in a high yield of about 95% each time.

The invention will be further described with reference to the following examples and comparison example.

EXAMPLE 1

A 1.22 g quantity of p-methyl anisole and 23.0 g of ammonium cerium(IV) nitrate are placed into a reactor, and 100 ml of methanol is further placed into the reactor. The mixture is stirred at room temperature for about 30 minutes. After the completion of the reaction, the methanol is distilled off from the reaction mixture. The residue is diluted with water and then subjected to extraction with benzene three times. The extract is washed with an aqueous solution of sodium chloride, dried over anhydrous sodium sulfate and distilled to remove the solvent. The residue is distilled in a vacuum, giving 1.308 g of anisaldehyde (b.p. 90°–92° C./2 mm Hg). Yield: 96.2%.

The aqueous layer resulting from the extraction is distilled to remove water and obtain ammonium cerium(III) nitrate, which is added to 100 ml of the recovered methanol. The methanol solution is placed into an anode chamber. A 100 ml quantity of methanol containing 6 g of ammonium nitrate dissolved therein is placed into a cathode chamber partitioned from the anode chamber by a porcelain diaphragm. With use of platinum electrodes, the cerium salt is electrolyzed with a constant current of 60 mA.

After the completion of the electrolysis, 1.23 g of p-methyl anisole is added to the solution withdrawn from the anode chamber, and the same procedure as above is thereafter repeated to obtain 1.30 g of anisaldehyde.

drawn from the anode chamber to give anisaldehyde in a yield of 94.8%.

EXAMPLES 13–16

The procedure of Example 1 is repeated similarly under the conditions listed in Table 2, using other alcohols in place of methanol. Table 2 also shows the results.

TABLE 2

| Example | Electrolytic reaction | | | | | Oxidation reaction | | |
|---|---|---|---|---|---|---|---|---|
| | Electrodes | | | Current | Quantity of electricity | Ammonium nitrate | | | |
| | (+) | (−) | Solvent | (mA) | (F/mole) | (g) | Temp. (°C.) | Time (hr) | Yield (%) |
| 13 | C | SUS | Ethanol | 60 | 1.2 | 6 | Room temp. | 0.5 | 94.3 |
| 14 | C | SUS | n-Propanol | 60 | 1.2 | 6 | Room temp. | 0.5 | 94.1 |
| 15 | C | SUS | i-Propanol | 60 | 1.2 | 6 | Room Temp. | 0.5 | 94.5 |
| 16 | C | SUS | n-Butanol | 60 | 1.2 | 6 | Room temp. | 0.5 | 92.9 |

EXAMPLES 2–10

The process of Example 1 is repeated similarly under the conditions listed in Table 1 below, regenerating the cerium salt for use in circulation. The results are shown in Table 1, in which "SUS" stands for stainless steel.

TABLE 1

| Example | Electrolytic reaction | | | | | Oxidation reaction | | |
|---|---|---|---|---|---|---|---|---|
| | Electrodes | | Current (mA) | Quantity of electricity (F/mole) | Ammonium nitrate (g) | Temp. (°C.) | Time (hr) | Yield (%) |
| | (+) | (−) | | | | | | |
| 2 | Pt | Pt | 60 | 1.2 | 6 | 40–50 | 0.5 | 95.6 |
| 3 | Pt | Pt | 60 | 1.1 | 6 | Room temp. | 0.5 | 96.5 |
| 4 | Pt | Pt | 60 | 1.0 | 6 | Room temp. | 0.5 | 96.7 |
| 5 | Pt | SUS | 60 | 1.2 | 6 | Room temp. | 0.5 | 95.9 |
| 6 | Pt | SUS | 60 | 1.1 | 6 | 0–10 | 0.5 | 97.0 |
| 7 | Pt | SUS | 60 | 1.0 | 6 | Room temp. | 0.5 | 95.9 |
| 8 | C | SUS | 60 | 1.2 | 6 | Room temp. | 0.5 | 96.1 |
| 9 | C | SUS | 60 | 1.1 | 6 | 30–40 | 0.5 | 96.3 |
| 10 | C | SUS | 60 | 1.0 | 6 | Room temp. | 0.5 | 95.9 |

EXAMPLE 11

The same procedure as in Example 1 is repeated except that the cerium salt is electrolyzed with 10 ml of 65% by weight aqueous solution of nitric acid placed into the cathode chamber in place of ammonium nitrate. p-Methyl anisole is oxidized with the solution withdrawn from the anode chamber to give anisaldehyde in a yield of 96.0%.

EXAMPLE 12

The same procedure as in Example 1 is repeated except that the cerium salt is electrolyzed with 100 ml of 2 to 3% by weight aqueous solution of nitric acid placed into the cathode chamber in place of ammonium nitrate. p-Methyl anisole is oxidized with the solution with-

EXAMPLE 17

In the same manner as in Example 1, p-methyl anisole is oxidized with use of an 80% by weight aqueous solution of methanol in place of methanol, affording anisaldehyde in a yield of 97.3%. With use of cerium salt regenerated in the same manner as in Example 1 (and using an 80% by weight methanol aqueous solution in place of methanol) for the second oxidation, anisaldehyde is obtained in a yield of 94.3%.

EXAMPLE 18

A methanol solution of 24.6 g of cerium(III) nitrate is placed into an anode chamber, and a methanol solution of 2 g of ammonium nitrate is placed into a cathode chamber. The cerium salt is electrolyzed with a constant current of 50 mA to pass electricity across the electrodes in a quantity of 1.2 F/mole. A 1.22 g quantity of p-methyl anisole is added to the solution withdrawn from the anode chamber after the electrolysis, and the mixture is stirred for 30 minutes. The same procedure as in Example 1 is thereafter repeated, giving 1.312 g of anisaldehyde. Yield: 96.5%.

EXAMPLE 19

The procedure of Example 1 is repeated with use of an ion exchange diaphragm in place of the porcelain diaphragm, giving anisaldehyde in a yield of 96.3%.

EXAMPLE 20

A 18.2 g quantity of cerium(III) nitrate is dissolved in 100 ml of methanol containing 10 ml of 65% by weight of nitric acid, and the solution is placed into an anode chamber. A methanol solution containing 10 ml of 65% by weight of nitric acid is placed into a cathode chamber. The cerium salt is electrolyzed with a constant current of 60 mA using platinum electrodes to pass electricity across the electrodes in a quantity of 1.2 F/mole. A 1.22 g of quantity of p-methyl anisole is oxidized with the solution withdrawn from the anode chamber after the electrolysis. The same procedure as in Example 1 is thereafter repeated to obtain 1.306 g of anisaldehyde. Yield: 96.0%.

EXAMPLE 21 p-Methyl anisole (1.22 g) and 23.0 g of ammonium cerium(IV) nitrate are placed into a reactor, and 100 ml of methanol is further placed thereinto. The mixture is stirred at room temperature for 30 minutes and thereafter distilled to remove the methanol. The residue is dissolved in benzene, and solids are separated from the solution. The solution is distilled to remove the benzene, and the residue is distilled in a vacuum, affording 1.31 g of anisaldehyde. Yield 96.3%. The separated solids are dissolved in the recovered methanol, and the solution is placed into an anode chamber. A methanol solution of 6 g of ammonium nitrate is placed into a cathode partitioned from the anode chamber by a diaphragm. The cerium salt is electrolyzed with a constant current of 60 mA, using platinum electrodes, to pass electricity across the electrodes in a quantity of 1.2 F/mole.

A 1.22 g quantity of p-methyl anisole is added to the solution withdrawn from the anode chamber after the electrolysis, and the same procedure as above is thereafter repeated to afford 1.32 g of anisaldehyde. Yield 97.1%.

EXAMPLE 22

A 1.22 g quantity of p-methyl anisole and 23.0 g of ammonium cerium(IV) nitrate are placed into a reactor, and 100 ml of methanol is further placed into the reactor. The mixture is stirred at room temperature for about 30 minutes. After the completion of the reaction, the methanol is distilled off from the reaction mixture. The residue is subjected to extraction with benzene three times. The extract is washed with an aqueous solution of sodium chloride, dried over anhydrous sodium sulfate and distilled to remove the solvent. The residue is distilled in a vacuum, giving 1.31 g of anisaldehyde. Yield 96.2%.

The solids obtained from the extraction residue is dissolved in 50 ml of water, and the solution is placed into an anode chamber. A 3% aqueous solution of nitric acid is placed into a cathode chamber partitioned from the anode chamber by an ion exchange diaphragm. With use of platinum electrodes, the cerium salt is electrolyzed with a constant current of 60 mA to pass electricity across the electrodes in a quantity of 1.2 F/mole. A 1.22 g quantity of p-methyl anisole is added to the solution withdrawn from the anode chamber after the electrolysis, and the same procedure as above is thereafter repeated to give 1.13 g of anisaldehyde. Yield 83.2%.

EXAMPLE 23

A 1.22 g quantity of p-methyl anisole and 23.0 g of ammonium cerium(IV) nitrate are placed into a reactor, and 100 ml of methanol is further placed into the reactor. The mixture is stirred at room temperature for about 30 minutes. After the completion of the reaction, the methanol is distilled off from the reaction mixture. The residue is subjected to extraction with benzene three times. The extract is washed with an aqueous solution of sodium chloride, dried over anhydrous sodium sulfate and distilled to remove the benzene. The residue is distilled in a vacuum, giving 1.32 g of anisaldehyde. Yield 96.8%.

The solids obtained from the extraction residue is dissolved in 100 ml of methanol, and the solution is placed into an anode chamber. An aqueous solution of 6 g of ammonium nitrate in the same amount as the solution in the anode chamber is placed into a cathode chamber partitioned from the anode chamber by an ion exchange diaphragm. With use of platinum electrodes, the cerium salt is electrolyzed with a constant current of 60 mA to pass electricity across the electrodes in a quantity of 1.2 F/mole. A 1.22 g quantity of p-methyl anisole is added to the solution withdrawn from the anode chamber after the electrolysis, and the same procedure as above is thereafter repeated to give 1.324 g of anisaldehyde. Yield 97.1%.

COMPARISON EXAMPLE 1

Into a reactor are placed 1.22 g of p-methyl anisole and 23.0 g of ammonium cerium(IV) nitrate, and 150 ml of water is further placed into the reactor. The mixture is stirred at room temperature for 6 hours. The same extraction and purification steps as in Example 1 are performed for the reaction mixture, affording anisaldehyde in a yield of 20% and a large amount of tar-like compound of unidentified structure.

We claim:

1. A process for preparing anisaldehyde characterized by performing at least once the steps of (a) electrolyzing cerium (III) nitrate or ammonium cerium (III) nitrate with use of a cathode chamber having contained therein nitrate ion-containing water and/or a nitrate ion-containing solution comprising a lower alcohol containing the cerium salt to obtain water containing cerium (IV) nitrate or ammonium cerium (IV) nitrate and/or a solution comprising a lower alcohol containing the cerium (IV) salt, and (b) oxidizing, at a temperature of about −10° to about 60° C., p-methyl anisole to anisaldehyde with the cerium (IV) salt-containing solution comprising a lower alcohol with or without the water contained therein, or with the cerium (IV) salt-containing water having a lower alcohol admixed therewith, the amount of said lower alcohol present in the cerium (IV) salt-containing solution, or in the cerium (IV) salt-containing water having a lower alcohol admixed therewith, being at least 20% by weight of the total amount of solvent.

2. A process as defined in claim 1 wherein the source of the nitrate ion is nitric acid, ammonium nitrate, sodium nitrate, potassium nitrate or an alkyl ammonium salt of nitric acid.

3. A process as defined in claim 2 wherein the nitrate ion source is nitric acid or ammonium nitrate.

4. A process as defined in claim 1 wherein the lower alcohol has 1 to 4 carbon atoms.

5. A process as defined in claim 1 wherein nitric acid or ammonium nitrate is admixed with the water containing the cerium(III) salt and/or the solution comprising a lower alcohol containing the cerium(III) salt for electrolysis.

6. A process as defined in claim 1 wherein said solution comprising a lower alcohol comprises a mixture of lower alcohol and organic solvent.

7. A process as claimed in claim 6 wherein said organic solvent is selected from the group consisting of ethers, nitriles, ketones, and esters.

8. A process as defined in claim 6 wherein the organic solvent is diethyl ether, tetrahydrofuran, dioxane, acetonitrile, propionitrile, dimethylformamide, dimethyl sulfoxide, acetone, methyl ethyl ketone, ethyl acetate or methyl propionate.

9. A process as defined in claim 1 wherein the cathode chamber is partitioned from the anode chamber by a diaphragm.

10. A process as defined in claim 1 wherein the oxidation reaction is conducted at about 0° to about 50° C.

11. A process as defined in claim 1 wherein the cerium(III) salt is electrolyzed at about 0° to about 100° C.

12. A process as defined in claim 11 wherein the electrolysis is conducted at about 10° to about 60° C.

* * * * *